United States Patent [19]
Audousset

[11] Patent Number: 5,814,106
[45] Date of Patent: Sep. 29, 1998

[54] COMPOSITION FOR THE OXIDATION DYEING OF KERATIN FIBRES CONTAINS A 4-HYDROXYINDOLINE COUPLER AT AN ACIDIC PH AND DYEING PROCESS USING THIS COMPOSITION

[75] Inventor: Marie-Pascale Audousset, Asnieres, France

[73] Assignee: L'Oreal, Paris, France

[21] Appl. No.: 836,897

[22] PCT Filed: Sep. 20, 1996

[86] PCT No.: PCT/FR96/01472

§ 371 Date: May 22, 1997

§ 102(e) Date: May 22, 1997

[87] PCT Pub. No.: WO97/11673

PCT Pub. Date: Mar. 3, 1997

[30] Foreign Application Priority Data

Sep. 25, 1995 [FR] France ................................... 95 11223

[51] Int. Cl.$^6$ ....................................................... A61K 7/13
[52] U.S. Cl. ......................... 8/409; 8/408; 8/410; 8/412; 8/423
[58] Field of Search ............................... 8/408, 409, 410, 8/412, 423

[56] References Cited

U.S. PATENT DOCUMENTS

| | | | |
|---|---|---|---|
| 4,013,404 | 3/1977 | Parent et al. | 8/423 |
| 5,391,206 | 2/1995 | Cotteret | 8/408 |

FOREIGN PATENT DOCUMENTS

| | | |
|---|---|---|
| A 428441 | 5/1991 | European Pat. Off. |
| A 465340 | 1/1992 | European Pat. Off. |
| A 1916139 | 11/1969 | Germany. |
| A 3031709 | 4/1982 | Germany. |
| 1217479 | 12/1970 | United Kingdom. |
| WO A 9309759 | 5/1993 | WIPO. |

OTHER PUBLICATIONS

Derwent Abstract of EP–A–428441, May 1991.

Derwent Abstract of DE–A–3031709, Apr. 1982.

*Primary Examiner*—Paul Lieberman
*Assistant Examiner*—Caroline L. Dusheck
*Attorney, Agent, or Firm*—Finnegan, Henderson, Farabow, Garrett & Dunner, L.L.P.

[57] ABSTRACT

The present invention relates to a ready-to-use composition for the oxidation dyeing of keratin fibers, in particular human keratin fibers such as the hair, this composition comprising, in an acidic medium (pH<7), at least one oxidation base, in combination with 4-hydroxyindoline as coupler, and an oxidizing agent, as well as to the dyeing process using this composition.

28 Claims, No Drawings

COMPOSITION FOR THE OXIDATION DYEING OF KERATIN FIBRES CONTAINS A 4-HYDROXYINDOLINE COUPLER AT AN ACIDIC PH AND DYEING PROCESS USING THIS COMPOSITION

The present invention relates to a ready-to-use composition for the oxidation dyeing of keratin fibres, in particular human keratin fibres such as the hair, this composition comprising, in an acidic medium (pH<7), at least one oxidation base, in combination with 4-hydroxyindoline as coupler, and an oxidizing agent, as well as to the dyeing process using this composition.

It is known to dye keratin fibres, and in particular human hair, with dye compositions containing oxidation dye precursors, in particular ortho- or para-phenylenediamines and ortho- or para-aminophenols, which are generally referred to as oxidation bases. Oxidation dye precursors, or oxidation bases, are colourless or weakly coloured compounds which, when combined with oxidizing products, may give rise to coloured compounds and dyes by a process of oxidative condensation.

It is also known that the shades obtained with these oxidation bases may be varied by combining them with couplers or coloration modifiers, these being chosen in particular from aromatic meta-diamines, meta-aminophenols, meta-diphenols and certain indole or indoline compounds.

The variety of molecules used as oxidation bases and couplers makes it possible to obtain a wide range of colours.

The so-called "permanent" coloration obtained by means of these oxidation dyes must moreover satisfy a certain number of requirements. Thus, it must have no toxicological drawbacks and it must allow shades of the desired intensity to be obtained and have good resistance to external agents (light, inclement weather, washing, permanent waving, perspiration and rubbing).

The dyes must also allow grey hair to be covered and, lastly, they must be as unselective as possible, that is to say that they must allow the smallest possible differences in coloration to be obtained over the entire length of the same keratin fibre, which may indeed be differently sensitized (i.e. damaged) between its tip and its root.

The oxidation dyeing of the keratin fibres is generally carried out in alkaline medium. However, alkaline media have the drawback of causing appreciable degradation of the fibres. By way of example, French patent application FR 2,008,797 has already proposed compositions for the oxidation dyeing of keratin fibres in alkaline medium, comprising at least one oxidation base and at least one indoline derivative as coupler.

The oxidation dyeing of keratin fibres may also be performed in acidic medium, in order to limit the degradation of the keratin fibres. However, the colorations obtained under these conditions are, unfortunately, generally less intense and not as fast as those obtained in alkaline medium.

Now, the Applicant has just discovered that it is possible to obtain novel dyes in acidic medium which are capable of giving rise to intense colorations, which are quite unselective and which suitably withstand the various attacks to which the hair may be subjected, by combining at least one oxidation base, 4-hydroxyindoline and an oxidizing agent such that the resulting ready-to-use mixture has a pH below 7.

This discovery forms the basis of the present invention.

The first subject of the invention is thus a ready-to-use composition for the oxidation dyeing of keratin fibres, and in particular human keratin fibres such as the hair, characterized in that it comprises, in a medium which is suitable for dyeing:

at least one oxidation base, 4-hydroxyindoline and/or at least one of the addition salts thereof with an acid, as coupler, at least one oxidizing agent, the pH of this ready-to-use composition being below 7.

The colorations obtained with the ready-to-use dye compositions in accordance with the invention are at least as intense as, if not more intense than, those of the prior art obtained with the same compositions used at basic pH, and they are moreover of low selectivity and have excellent properties of resistance both to atmospheric agents such as light and inclement weather and to perspiration and the various treatments to which the hair may be subjected (washing, permanent waving).

The subject of the invention is also a process for the oxidation dyeing of keratin fibres using this ready-to-use dye composition.

The oxidation bases which may be used in the ready-to-use compositions in accordance with the invention are preferably chosen from para-phenylenediamines, bis (phenyl)alkylenediamines, para-aminophenols, ortho-aminophenols and heterocyclic bases, and the addition salts thereof with an acid.

The addition salts with an acid which may be used in the context of the dye compositions of the invention (oxidation bases and 4-hydroxyindoline) are chosen in particular from the hydrochlorides, hydrobromides, sulphates and tartrates.

Among the para-phenylenediamines which may be used as oxidation bases in the context of the ready-to-use compositions in accordance with the invention, mention may be made in particular of the compounds corresponding to formula (I) below, and the addition salts thereof with an acid:

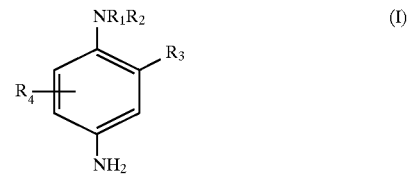

in which:

R$_1$ represents a hydrogen atom or a C$_1$–C$_4$ alkyl, C$_1$–C$_4$ monohydroxyalkyl, C$_2$–C$_4$ polyhydroxyalkyl, (C$_1$–C$_4$) alkoxy(C$_1$–C$_4$)alkyl, phenyl or 4'-aminophenyl radical, R$_2$ represents a hydrogen atom or a C$_1$–C$_4$ alkyl, C$_1$–C$_4$ monohydroxyalkyl or C$_2$–C$_4$ polyhydroxyalkyl radical, R$_3$ represents a hydrogen atom, a halogen atom such as a chlorine, bromine, iodine or fluorine atom or a C$_1$–C$_4$ alkyl, C$_1$–C$_4$ monohydroxyalkyl or C$_1$–C$_4$ hydroxyalkoxy radical, R$_4$ represents a hydrogen atom or a C$_1$–C$_4$ alkyl radical.

Among the para-phenylenediamines of formula (I) above, mention may be made more particularly of para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-3-methylaniline, 4-amino- 3-chloro-N,N-bis (β-hydroxyethyl)aniline, 4-amino-N-(β-methoxyethyl) aniline, 2-β-hydroxyethyl-para-phenylenediamine, 2-fluoropara-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine and 2-β-hydroxyethyloxy-para-phenylenediamine, and the addition salts thereof with an acid.

Among the para-phenylenediamines of formula (I) above, para-phenylenediamine, para-toluylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 4-amino-N-(β-methoxyethyl)aniline and 2-chloropara-phenylenediamine, and the addition salts thereof with an acid, are most particularly preferred.

Among the bis(phenyl)alkylenediamines which may be used as oxidation bases in the context of the ready-to-use compositions in accordance with the invention, mention may be made in particular of the compounds corresponding to formula (II) below, and the addition salts thereof with an acid:

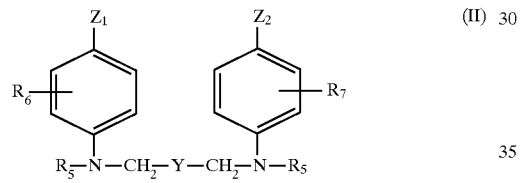

in which:
$Z_1$ and $Z_2$, which may be identical or different, represent a hydroxyl radical or a radical $NHR_8$ in which $R_8$ represents a hydrogen atom or a $C_1-C_4$ alkyl radical, $R_5$ represents a hydrogen atom, a $C_1-C_4$ alkyl, $C_1-C_4$ monohydroxyalkyl or $C_2-C_4$ polyhydroxyalkyl radical or a $C_1-C_4$ aminoalkyl radical in which the amino residue may be substituted, $R_6$ and $R_7$, which may be identical or different, represent a hydrogen or halogen atom or a $C_1-C_4$ alkyl radical, Y represents a radical taken from the group consisting of the following radicals:

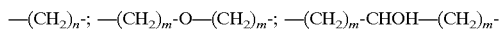

and

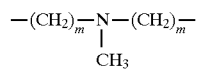

in which n is an integer from 0 to 8 and m is an integer from 0 to 4.

Among the bis(phenyl)alkylenediamines of formula (II) above, mention may be made more particularly of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine and N,N'-bis(ethyl)-N,N'-bis(4'-amino-3'-methylphenyl)ethylenediamine, and the addition salts thereof with an acid.

Among these bis(phenyl)alkylenediamines of formula (II), N,N'-bis(β-hydroxyethyl)-N,N'-bis(4'-aminophenyl)-1,3-diaminopropanol, or one of the addition salts thereof with an acid, is particularly preferred.

Among the para-aminophenols which may be used as oxidation bases in the context of the ready-to-use compositions in accordance with the invention, mention may be made in particular of the compounds corresponding to formula (III) below, and the addition salts thereof with an acid:

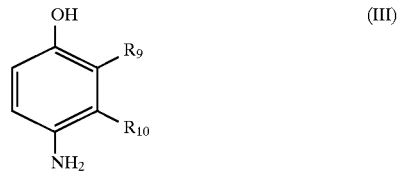

in which: p1 $R_9$ represents a hydrogen atom or a $C_1-C_4$ alkyl, $C_1-C_4$ monohydroxyalkyl, $(C_1-C_4)$ alkoxy$(C_1-C_4)$ alkyl or $C_1-C_4$ aminoalkyl radical, $R_{10}$ represents a hydrogen or fluorine atom or a $C_1-C_4$ alkyl, $C_1-C_4$ monohydroxyalkyl, $C_2-C_4$ polyhydroxyalkyl, $C_1-c_4$ aminoalkyl, $C_1-C_4$ cyanoalkyl or $(C_1-C_4)$alkoxy-$(C_1-C_4)$alkyl radical, it being understood that at least one of the radicals $R_9$ or $R_{10}$ represents a hydrogen atom.

Among the para-aminophenols of formula (III) above, mention may be made more particularly of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol and 4-amino-2-(β-hydroxyethylaminomethyl)phenol, and the addition salts thereof with an acid.

Among the ortho-aminophenols which may be used as oxidation bases in the context of the ready-to-use compositions of the invention, mention may be made more particularly of 2-aminophenol, 2-amino-5-methylphenol, 2-amino-6-methylphenol and 5-acetamido-2-aminophenol, and the addition salts thereof with an acid.

Among the heterocyclic bases which may be used as oxidation bases in the context of the ready-to-use compositions in accordance with the invention, there may more particularly be mentioned pyridine derivatives, pyrimidine derivatives, pyrazole derivatives, and the addition salts thereof with an acid.

Among the pyridine derivatives which may more particularly be mentioned are the compounds described, for example, in GB patents 1,026,978 and 1,153,196, such as 2,5-diaminopyridine, and the addition salts thereof with an acid.

Among the pyrimidine derivatives which may more particularly be mentioned are the compounds described, for example, in German patent DE 2,359,399 or Japanese patents JP 88-169,571 and JP 91-333,495, such as 2,4,5,6-tetraaminopyrimidine and 4-hydroxy-2,5,6-triaminopyrimidine, and the addition salts thereof with an acid.

Among the pyrazole derivatives which may more particularly be mentioned are the compounds described in patents DE 3,843,892 and DE 4,133,957 and patent applications WO 94/08969 and WO 94/08970, such as 4,5-diamino-1-methylpyrazole, 3,4-diaminopyrazole and 4,5-diamino-1-(4'-chlorobenzyl)pyrazole, and the addition salts thereof with an acid.

The oxidation base or bases preferably represent approximately from 0.0005 to 12% by weight relative to the total weight of the dye composition, and even more preferably approximately from 0.005 to 6% by weight.

The 4-hydroxyindoline and/or the addition salts thereof with an acid preferably represent(s) approximately from 0.0005 to 5% by weight relative to the total weight of the dye composition, and even more preferably approximately from 0.005 to 3% by weight.

According to an essential characteristic of the present invention, the pH of the ready-to-use dye composition in accordance with the invention is below 7 and may preferably range from 3 to 6.9. It may be adjusted to the desired value using acidifying or optionally basifying agents which are commonly used in the dyeing of keratin fibres.

Among the acidifying agents which may be mentioned, by way of example, are inorganic or organic acids such as hydrochloric acid, orthophosphoric acid, carboxylic acids such as tartaric acid, citric acid and lactic acid, and sulphonic acids.

Among the basifying agents which may be mentioned, by way of example, are aqueous ammonia, alkaline carbonates, alkanolamines such as mono-, di- and triethanolamine and derivatives thereof, sodium hydroxide, potassium hydroxide and the compounds of formula (IV) below:

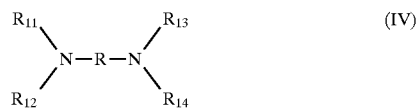

in which R is a propylene residue optionally substituted with a hydroxyl group or a $C_1$–$C_4$ alkyl radical; $R_{11}$, $R_{12}$, $R_{13}$ and $R_{14}$, which may be identical or different, represent a hydrogen atom or a $C_1$–$C_4$ alkyl or $C_1$–$C_4$ hydroxyalkyl radical.

The oxidizing agent present in the ready-to-use dye composition in accordance with the invention may be chosen from the oxidizing agents conventionally used in oxidation dyeing, and preferably from hydrogen peroxide, urea peroxide, alkali metal bromates and persalts such as perborates and persulphates. Hydrogen peroxide is particularly preferred.

In addition to the dyes defined above, the ready-to-use dye composition in accordance with the invention may also contain other couplers and/or direct dyes, in particular to modify the shades or to enrich them with glints.

The appropriate medium for dyeing (or support) for the dye compositions generally consists of water or of a mixture of water and at least one organic solvent to solubilize the compounds which would not be sufficiently soluble in water. Organic solvents which may be mentioned, for example, are $C_1$–$C_4$ lower alkanols such as ethanol and isopropanol; glycerol; glycols and glycol ethers such as 2-butoxyethanol, propylene glycol, propylene glycol monomethyl ether, diethylene glycol monomethyl ether and monoethyl ether, as well as aromatic alcohols such as benzyl alcohol or phenoxyethanol, similar products and mixtures thereof.

The solvents may be present in proportions preferably of approximately between 1 and 40% by weight relative to the total weight of the dye composition, and even more preferably of approximately between 5 and 30% by weight.

The ready-to-use dye compositions in accordance with the invention may also include various adjuvants used conventionally in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetration agents, sequestering agents, fragrances, buffers, dispersing agents, conditioners, film-forming agents, preserving agents and opacifying agents.

Obviously, a person skilled in the art will take care to choose this or these optional complementary compound(s) such that the advantageous properties intrinsically associated with the ready-to-use composition in accordance with the invention are not, or are substantially not, adversely affected by the addition or additions envisaged.

The ready-to-use dye compositions in accordance with the invention may be in various forms, such as in the form of liquids, creams, gels or any other form which is suitable for dyeing keratin fibres, and in particular human hair.

Another subject of the invention is a process for dyeing keratin fibres, and in particular human keratin fibres such as the hair, using the ready-to-use dye composition as defined above.

According to this process, at least one ready-to-use dye composition as defined above is applied to the fibres and is left to stand on the fibres for 3 to 50 minutes approximately, preferably 5 to 30 minutes approximately, after which the fibres are rinsed, optionally washed with shampoo, rinsed again and dried.

According to a preferred embodiment, the process includes a first step consisting in separately storing, on the one hand, a composition (A) comprising, in a medium which is suitable for dyeing, at least one oxidation base and 4-hydroxyindoline and/or at least one of the addition salts thereof with an acid, and, on the other hand, a composition (B) containing, in a medium which is suitable for dyeing, at least one oxidizing agent, for example such as defined above, and then in mixing them together at the time of use, before applying this mixture to the keratin fibres, the pH of the compositions (A) and (B) being such that after mixing from 10 to 90% of composition (A) with 90 to 10% of composition (B), the pH of the resulting mixture is below 7.

The pH of compositions (A) and (B) may be adjusted to the desired value using conventional acidifying or optionally basifying agents as defined above.

Another subject of the invention is a multi-compartment dyeing device or "kit" or any other multi-compartment packaging system, a first compartment of which contains composition (A) as defined above and a second compartment of which contains the oxidizing composition (B) as defined above. These devices may be equipped with a means which makes it possible to apply the desired mixture to the hair, such as the devices described in patent FR-2,586,913 in the name of the Applicant.

The examples which follow are intended to illustrate the invention without, however, limiting the scope thereof.

EXAMPLES

The following dye compositions 1 (A) and 2 (A) in accordance with the invention were prepared (contents in grams):

| COMPOSITION | 1 (A) | 2 (A) |
|---|---|---|
| Para-toluylenediamine | 0.584 | |
| 2,6-Dimethyl-para-phenylenediamine dihydrochloride | | 0.627 |
| 4-Hydroxyindoline | 0.405 | 0.405 |
| Common dye support (*) | (*) | (*) |
| Water qs | 100 g | 100 g |

(*) Common dye support:

-continued

| COMPOSITION | 1 (A) | 2 (A) |
|---|---|---|

Oleyl alcohol polyglycerolated with 2 mol of glycerol 4.0 g
Oleyl alcohol polyglycerolated with 4 mol of glycerol, containing 78% of active materials (AM) 5.69 g AM
Oleic acid 3.0 g
Oleylamine containing 2 mol of ethylene oxide, sold under the trade name Ethomeen O12 by the company AKZO 7.0 g
Diethylaminopropyl laurylaminosuccinamate, sodium salt, containing 55% of AM 3.0 g AM
Oleyl alcohol 5.0 g
Oleic acid diethanolamide 12.0 g
Propylene glycol 3.5 g
Ethyl alcohol 7.0 g
Dipropylene glycol 0.5 g
Propylene glycol monomethyl ether 9.0 g
Sodium metabisulphite in aqueous solution, containing 35% of AM 0.455 g AM
Ammonium acetate 0.8 g
Antioxidant, sequestering agent qs
Fragrance, preserving agent qs
Monoethanolamine qs pH 9.8

Each dye composition 1 (A) and 2 (A) was mixed, at the time of use, with an equal weight amount of an oxidizing composition (B) consisting of 20-volumes aqueous hydrogen peroxide solution (6% by weight) whose pH was adjusted to between 1 and 1.5 with 2.5 g of orthophosphoric acid per 100 g of aqueous hydrogen peroxide.

Each resulting composition had a pH below 7, and was applied for 30 minutes to locks of permanent-waved grey hair containing 90% white hairs. The locks of hair were then rinsed, washed with a standard shampoo and then dried.

Composition 1' (A) and 2' (A) were also prepared. These compositions 1' (A) and 2' (A) differed from the compositions 1 (A) and 2 (A) only in that the monoethanolamine used to adjust the pH of the dye composition (see the common dye support defined above) was replaced with 10 g of aqueous ammonia containing 20% of $NH_3$.

Each dye composition 1' (A) and 2' (A) was mixed, at the time of use, with an equal weight amount of an oxidizing composition (B') consisting of 20-volumes aqueous hydrogen peroxide solution (6% by weight) of pH 3.

Each resulting composition (not forming part of the invention) had a pH above 7, and was applied for 30 minutes to locks of permanent-waved grey hair containing 90% white hairs. The locks of hair were then rinsed, washed with a standard shampoo and then dried.

The colour of the locks was then evaluated in the Munsell system using a Minolta CM 2002 calorimeter.

According to the Munsell notation, a colour is defined by the expression HV/C in which the three parameters respectively denote the shade or Hue (H), the intensity or Value (V) and the purity or Chromaticity (C), the oblique line in this expression simply being a convention and not indicating a ratio.

The difference between the colour of the locks before and after dyeing was calculated by applying the Nickerson formula:

$$\Delta E = 0.4 \, C_0 \Delta H + 6 \Delta V + 3 \Delta C,$$

as described, for example, in "Couleur, Industrie et Technique"; pages 14–17; vol. No. 5; 1978.

In this formula, ΔE represents the difference in colour between two locks, ΔH, ΔV and ΔC represent the variation in absolute value of the parameters H, V and C, and $C_0$ represents the purity of the lock relative to which it is desired to evaluate the colour difference.

ΔE thus reflects the intensity of the coloration obtained, which is proportionately greater the higher the value of ΔE.

The colour of the locks before dyeing was:

4.3 Y 4.9/1.4 and thus $C_0 = 1.4$.

The results are given in the table below:

| EXAMPLE [Composition] | pH of the mixture applied to the hair | Colour of the lock after dyeing | Intensity of the coloration | | | |
|---|---|---|---|---|---|---|
| | | | ΔH | ΔV | ΔC | ΔE |
| 1[1 (A)] | 6.9 | 7.8 YR 2.1/0.5 | 6.5 | 2.8 | 0.9 | 23.1 |
| 1' [1' (A)] | 9.9 | 5.2 YR 2.6/1.1 | 9.1 | 2.3 | 0.3 | 19.8 |
| 2[2 (A)] | 6.9 | 8.6 YR 2.3/0.3 | 5.7 | 2.6 | 1.1 | 22.1 |
| 2'[2' (A)] | 9.9 | 4.6 YR 2.7/0.8 | 9.7 | 2.2 | 0.6 | 20.4 |

These results show that when the dyeing is performed with the ready-to-use dye compositions in accordance with the invention, that is to say those in which the pH is below 7 (ready-to-use dye compositions of Examples 1 and 2), it leads to colorations which are more intense than those obtained with the ready-to-use dye compositions not forming part of the invention (ready-to-use dye compositions of Examples 1' and 2') which have a pH above 7.

I claim:

1. A ready-to-use composition for the oxidation dyeing of keratin fibres, said composition comprising, in a medium which is suitable for dyeing, at least one oxidation base; 4-hydroxyindoline and/or at least one acid addition salt thereof as a coupler; and at least one oxidizing agent, wherein the pH of said composition is below 7.

2. A composition according to claim 1, wherein said keratin fibres are human keratin fibres.

3. A composition according to claim 1, wherein said at least one oxidation base is a para-phenylenediamine, a bis(phenyl)alkylene-diamine, a para-aminophenol, an ortho-aminophenol, a heterocyclic base, or an acid addition salt of one of said compounds.

4. A composition according to claim 3, wherein said para-phenylenediamine is a compound of formula (I) or an acid addition salt thereof:

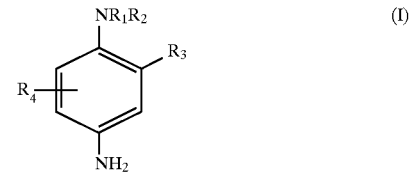

in which:

$R_1$ represents a hydrogen atom or a $C_1$–$C_4$ alkyl, $C_1$–$C_4$ monohydroxyalkyl, $C_2$–$C_4$ polyhydroxyalkyl, ($C_1$–$C_4$) alkoxy($C_1$–$C_4$)alkyl, phenyl or 4'-aminophenyl radical;

$R_2$ represents a hydrogen atom or a $C_1$–$C_4$ alkyl, $C_1$–$C_4$ monohydroxyalkyl or $C_2$–$C_4$ polyhydroxyalkyl radical;

$R_3$ represents a hydrogen atom, a halogen atom, or a $C_1$–$C_4$ alkyl, $C_1$–$C_4$ monohydroxyalkyl or $C_1$–$C_4$ hydroxyalkoxy radical; and $R_4$ represents a hydrogen atom or a $C_1$–$C_4$ alkyl radical.

5. A composition according to claim 4, wherein said halogen atom is a chlorine, bromine, iodine or fluorine atom.

6. A composition according to claim 4, wherein said para-phenylenediamine of formula (I) is para-phenylenediamine, para-toluylenediamine, 2-chloropara-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N, N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-3-methylaniline, 4-amino-3-chloro-N, N-bis (β-hydroxyethyl)-aniline, 4-amino-N-(β-methoxyethyl) aniline, 2-β-hydroxyethyl-para-phenylenediamine, 2-fluoropara-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, or an acid addition salt of one of said compounds.

7. A composition according to claim 6, wherein said para-phenylenediamine of formula (I) is para-phenylenediamine, para-toluylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 4-amino-N-(β-methoxyethyl)aniline, 2-chloropara-phenylenediamine, or an acid addition salt of one of said compounds.

8. A composition according to claim 3, wherein said bis(phenyl)alkylenediamine is a compound of formula (II) or an acid addition salt thereof:

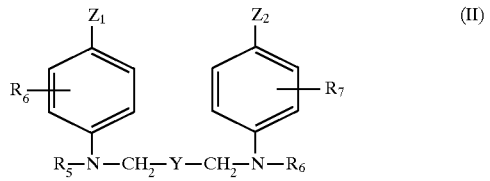

in which:

$Z_1$ and $Z_2$, which may be identical or different, represent a hydroxyl radical or a radical $NHR_8$ in which $R_8$ represents a hydrogen atom or a $C_1$–$C_4$ alkyl radical;

$R_5$ represents a hydrogen atom, a $C_1$–$C_4$ alkyl, $C_1$–$C_4$ monohydroxyalkyl or $C_2$–$C_4$ polyhydroxyalkyl radical or a $C_1$–$C_4$ aminoalkyl radical in which the amino residue is optionally substituted;

$R_6$ and $R_7$, which may be identical or different, represent a hydrogen or halogen atom or a $C_1$–$C_4$ alkyl radical;

Y represents a radical selected from the group consisting of the following radicals:

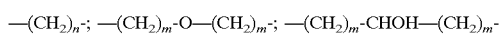

and

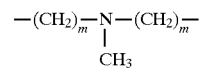

in which n is an integer ranging from 0 to 8 and m is an integer ranging from 0 to 4.

9. A composition according to claim 8, wherein said bis(phenyl)alkylenediamine is a N,N'-bis(β-hydroxyethyl)-N,N'-bis(4'-aminophenyl)-1,3-diaminopropanol, N,N'-bis(β-hydroxyethyl)-N,N'-bis(4'-aminophenyl) ethylenediamine, N,N'-bis(4-aminophenyl) tetramethylenediamine, N,N'-bis(β-hydroxyethyl)-N,N'-bis(4-aminophenyl)-tetramethylenediamine, N,N'-bis(4-methylaminophenyl)tetramethylenediamine, N,N'-bis(ethyl)-N,N'-bis(4'-amino-3'-methylphenyl)ethylenediamine, or an acid addition salt of one of said compounds.

10. A composition according to claim 9, wherein said bis(phenyl)alkylenediamine is N,N'-bis(β-hydroxyethyl)-N,N'-bis(4'-aminophenyl)-1,3-diaminopropanol or an acid addition salt thereof.

11. A composition according to claim 3, wherein said para-aminophenol is a compound of formula (III) or an acid addition salt thereof:

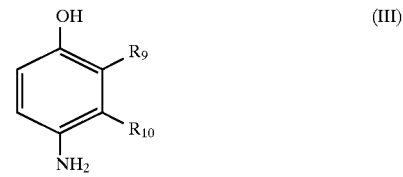

in which:

$R_9$ represents a hydrogen atom or a $C_1$–$C_4$ alkyl, $C_1$–$C_4$ monohydroxyalkyl, $(C_1$–$C_4)$alkoxy$(C_1$–$C_4)$alkyl or $C_1$–$C_4$ aminoalkyl radical; and $R_{10}$ represents a hydrogen or fluorine atom or a $C_1$–$C_4$ alkyl, $C_1$–$C_4$ monohydroxyalkyl, $C_2$–$C_4$ polyhydroxyalkyl, $C_1$–$C_4$ aminoalkyl, $C_1$–$C_4$ cyanoalkyl or $(C_1$–$C_4)$alkoxy-$(C_1$–$C_4)$alkyl radical; wherein at least one of the radicals $R_9$ or $R_{10}$ represents a hydrogen atom.

12. A composition according to claim 11, wherein said para-aminophenol is para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, or an acid addition salt of one of said compounds.

13. A composition according to claim 3, wherein said ortho-aminophenol is 2-aminophenol, 2-amino-5-methylphenol, 2-amino-6-methylphenol, 5-acetamido-2-aminophenol, or an acid addition salt of one of said compounds.

14. A composition according to claim 3, wherein said heterocyclic base is a pyridine derivative, a pyrimidine derivative, a pyrazole derivative, or an acid addition salt of one of said compounds.

15. A composition according to claim 14, wherein said heterocyclic base is 2,4,5,6-tetraaminopyrimidine, 2,5-diaminopyridine, 4,5-diamino-1-methylpyrazole, 3,4-diaminopyrazole, 4,5-diamino-1-(4'-chlorobenzyl)-pyrazole, 4-hydroxy-2,5,6-triaminopyrimidine, or an acid addition salt of one of said compounds.

16. A composition according to claim 1, wherein said at least one acid addition salt is a hydrochloride, hydrobromide, sulphate or tartrate.

17. A composition according to claim 1, wherein said at least one oxidation base represents from 0.0005 to 12% by weight relative to the total weight of the dye composition.

18. A composition according to claim 17, wherein said at least one oxidation base represents from 0.005 to 6% by weight relative to the total weight of the dye composition.

19. A composition according to claim 1, wherein said 4-hydroxyindoline and/or said at least one acid addition salt thereof represents from 0.0005 to 5% by weight relative to the total weight of the dye composition.

20. A composition according to claim 19, wherein said 4-hydroxyindoline and/or said at least one acid addition salt thereof represents from 0.005 to 3% by weight relative to the total weight of the dye composition.

21. A composition according to claim 1, wherein said pH ranges from 3 to 6.9.

22. A composition according to claim 1, wherein said at least one oxidizing agent is hydrogen peroxide, urea peroxide, an alkali metal bromate or a persalt.

23. A composition according to claim 22, wherein said persalt is a perborate or a persulphate.

24. A process for dyeing keratin fibres, said process comprising applying at least one ready-to-use dye composition according to claim 1 to said fibres.

25. A process according to claim 24, wherein said keratin fibres are human keratin fibres.

26. A process according to claim 25, wherein said human keratin fibres are hair.

27. A process according to claim 24, said process comprising:

separately storing a composition (A) and a composition (B), said composition (A) comprising, in a medium suitable for dyeing, at least one oxidation base and 4-hydroxyindoline and/or at least one acid addition salt thereof, said composition (B) comprising, in a medium suitable for dyeing, at least one oxidizing agent;

combining, just prior to the time of application, from 10 to 90% of said composition (A) with from 10 to 90% of said composition (B) to form a mixture, said mixture having a pH below 7; and applying said mixture to said keratin fibres.

28. A multi-compartment dyeing device, which comprises at least two compartments, wherein a first compartment contains a composition (A) comprising, in a medium suitable for dyeing, at least one oxidation base and 4-hydroxyindoline and/or at least one acid addition salt thereof, and a second compartment contains a composition (B) comprising, in a medium suitable for dyeing, at least one oxidizing agent, said compositions (A) and (B) having pH's such that when combining 10 to 90% of said composition (A) with from 10 to 90% of said composition (B) to form a mixture, said mixture has a pH below 7.

* * * * *